US011464626B2

(12) United States Patent
Fahl

(10) Patent No.: US 11,464,626 B2
(45) Date of Patent: Oct. 11, 2022

(54) INSERTION AID FOR VOICE PROSTHESES

(71) Applicant: Andreas Fahl Medizintechnik—Vertrieb GmbH, Cologne (DE)

(72) Inventor: Andreas Fahl, Cologne (DE)

(73) Assignee: Andreas Fahl Medizintechnik—Vertrieb GmbH, Cologne (DE)

( * ) Notice: Subject to any disclaimer, the term of this patent is extended or adjusted under 35 U.S.C. 154(b) by 422 days.

(21) Appl. No.: 16/489,830

(22) PCT Filed: Feb. 22, 2018

(86) PCT No.: PCT/EP2018/054333
§ 371 (c)(1),
(2) Date: Jun. 11, 2020

(87) PCT Pub. No.: WO2018/153952
PCT Pub. Date: Aug. 30, 2018

(65) Prior Publication Data
US 2020/0368013 A1 Nov. 26, 2020

(30) Foreign Application Priority Data

Feb. 22, 2017 (DE) .......................... 102017103623.7

(51) Int. Cl.
*A61F 2/20* (2006.01)
(52) U.S. Cl.
CPC ................... *A61F 2/203* (2013.01)
(58) Field of Classification Search
CPC ..................................... A61F 2/203
USPC ............................................. 623/9
See application file for complete search history.

(56) References Cited

U.S. PATENT DOCUMENTS

| 5,064,433 | A | 11/1991 | Blom et al. |
| 5,935,165 | A | 8/1999 | Schouwenburg |
| 8,332,999 | B2* | 12/2012 | Karling ................... A61F 2/203 29/243.5 |
| 9,675,446 | B2* | 6/2017 | Jaber ......................... A61F 2/20 |
| 9,675,448 | B2* | 6/2017 | Fagan ..................... A61F 2/203 |
| 10,413,399 | B2* | 9/2019 | Blom ......................... A61F 2/20 |
| 11,202,703 | B2* | 12/2021 | Kaufman ................. A61F 2/20 |
| 2009/0036983 | A1* | 2/2009 | Tran ........................ A61F 2/203 623/9 |

(Continued)

FOREIGN PATENT DOCUMENTS

DE 69607767 T2 8/2000
DE 202008000670 U1 4/2008

OTHER PUBLICATIONS

International Search Report dated May 25, 2018; International Application No. PCT/EP2018/054333.

*Primary Examiner* — Suzette J Gherbi
(74) *Attorney, Agent, or Firm* — Dinsmore & Shohl LLP

(57) ABSTRACT

To achieve the object of making available an insertion aid for a voice prosthesis, which insertion aid can be used universally and permits a secure hold on the voice prosthesis, such an insertion aid is proposed comprising a rod-shaped device with a head region arranged at a first end of a rod, said head region comprising a limit stop element for a voice prosthesis and, adjoining this limit stop element, a locking element for a voice prosthesis, wherein a first ring surface is formed between the limit stop element and the locking element, which ring surface is configured extending radially with respect to a longitudinal axis of the rod.

17 Claims, 8 Drawing Sheets

(56) References Cited

U.S. PATENT DOCUMENTS

| | | | |
|---|---|---|---|
| 2009/0043386 A1 | 2/2009 | Persson | |
| 2009/0102180 A1* | 4/2009 | Karling | A61F 2/203 |
| | | | 285/20 |
| 2011/0093071 A1 | 4/2011 | Blom | |
| 2012/0215306 A1* | 8/2012 | Fagan | A61F 2/203 |
| | | | 623/9 |
| 2013/0274876 A1* | 10/2013 | Blom | A61F 2/203 |
| | | | 623/9 |
| 2015/0094809 A1* | 4/2015 | Perrin | A61F 2/04 |
| | | | 623/9 |
| 2016/0228239 A1* | 8/2016 | Perrin | A61F 2/20 |
| 2019/0336276 A1* | 11/2019 | Kamradt | A61F 2/203 |
| 2020/0008933 A1* | 1/2020 | Kaufman | A61F 2/20 |

* cited by examiner

INSERTION AID FOR VOICE PROSTHESES

CROSS-REFERENCE TO RELATED APPLICATIONS

This application is the U.S. national stage of PCT/EP2018/054333 filed Feb. 22, 2018, which claims priority of German Patent Application 102017103623.7 filed Feb. 22, 2017 of which both are hereby incorporated by reference in its entirety.

FIELD OF THE INVENTION

The present invention relates to an insertion aid for a voice prosthesis comprising a rod-shaped device and a sleeve, as well as the use thereof.

BACKGROUND OF THE INVENTION

Voice prostheses are used to restore the voice during or after a laryngectomy. The restoration of the voice can take place through surgery. The most important resource for this is the voice prosthesis, which can also be referred to as a "shunt" valve. The functions of the removed larynx can be replaced by a voice prosthesis. An air passage from the lungs to the pharynx via the esophagus is created through the use of a voice prosthesis. The exhalation air is then used for speaking. The voice prosthesis also seals the connection from the esophagus to the trachea when swallowing food and drink, by means of which the user of the voice prosthesis is protected against accidentally inhaling the food or drink.

If the voice prosthesis is a permanent prosthesis, it is normally inserted or replaced by a physician. These permanent prostheses are placed in the so-called tracheoesophageal fistula, a surgical opening between the trachea and the esophagus. The voice is obtained by closing the tracheostoma with a finger and exhaling at the same time. The valve in the voice prosthesis is then opened by the resulting pressure and allows air to enter the esophagus, thus forming a sound for the voice.

Voice prostheses in the form of permanent prostheses have two flanges, between which a shaft is formed. The inner surfaces of the flanges facing the shaft of the more or less rotationally symmetrical voice prosthesis bear on either a surface of the trachea or a surface of the esophagus. The shaft in such a voice prosthesis is located in the surgical opening, the tracheoesophageal fistula. Because the flanges have a greater diameter than the shaft, it is difficult to insert such a voice prosthesis in the form of a permanent prosthesis. An aid for inserting such a voice prosthesis into the tracheoesophageal fistula is disclosed in DE 696 07 767 T2. A voice prosthesis like that described above is placed on an insertion element in that it is placed on a cylindrical head on one end of the insertion element. The cylindrical head is slightly conical. Using a fastening nipple located on the flange that comes to bear on a wall of the esophagus, the voice prosthesis is retained on the insertion element through a keyhole opening, into which the fastening nipple is inserted. The problem with this insertion aid is that the voice prosthesis sits loosely on the head of the insertion element, such that when the fastening nipple is placed in the keyhole opening, thus stretching the material of the fastening nipple, normally made of medical silicone, the voice prosthesis can slip or separate from the head. It may also be possible for the voice prosthesis to become damaged, and thus unusable.

Other voice prostheses are known from the prior art beside that in DE 696 07 767 T2. There are those that likewise have a fastening nipple, although it is not retained in a keyhole opening in an insertion element, but instead is placed on an insertion element in the form of a rod, and is connected to the insertion element after placing the voice prosthesis on a cylindrical retaining region on one end of the insertion element, in which the fastening nipple is fastened to a projection on the insertion element with a hole in the nipple. This also results in a loose attachment of the voice prosthesis to the cylindrical end region of the insertion element, such that it too can become skewed, slide off, or possibly even damage the voice prosthesis.

U.S. Pat. No. 5,064,433 A describes a voice prosthesis with an insertion aid, wherein the voice prosthesis has a fastening means, and the insertion aid has an integrally and homogenously formed fastening means thereon, in order to releasably connect the device to the tool.

US 2011/093071 A1 describes a method for inserting a voice prosthesis by means of a gel cap.

U.S. Pat. No. 5,935,165 describes an insertion aid with a receiver that can be spread open to receive a voice prosthesis.

US 2009/043386 A1 describes a voice prosthesis and an insertion aid adapted to one another.

DE 20 2008 000 670 U1 describes an insertion device with a guide wire channel.

Because a number of different voice prostheses are fundamentally known from the prior art, each of which has a specific insertion element, the user is in the difficult situation of having to keep a number of different insertion elements available for when different voice prostheses are used.

SUMMARY OF THE INVENTION

The present invention addresses the problem of creating an insertion aid for voice prostheses that can be used universally, i.e. independently of the designs of the voice prostheses known from the prior art, enabling a secure retention of the voice prosthesis on the aid.

This problem is solved according to the invention by an insertion aid for a voice prosthesis that comprises a rod-shaped device with a head region on a first end of the rod that comprises a stop element for a voice prosthesis and an adjoining retention element in the form of an inverted truncated cone for a voice prosthesis, wherein a first annular surface is formed between this stop element and the retention element, which extends radially in relation to the longitudinal axis of the rod. The insertion aid according to the invention offers the major advantage that a voice prosthesis located on the rod-shaped device is securely retained thereon, specifically in a locked, i.e. fixed position in the head region of the rod-shaped device. As a result, the voice prosthesis cannot slip or wobble, or become damaged. The region of the voice prosthesis that the retention element comes in contact with is normally made of a flexible, elastic material, such as medical silicone. The retention element on the rod-shaped device comes in contact with an inner wall of the voice prosthesis when the voice prosthesis is placed on the head region of the rod, stretching it slightly. This stretching function of the retention element is obtained with a very small surface thereof that comes in contact with the inner wall of the voice prosthesis in order to avoid damaging it, and to also enable an easy removal of the rod-shaped device from the inserted voice prosthesis after it has been inserted in the tracheoesophageal fistula. If this were a large surface, it would be more difficult to remove the rod-shaped device, or it would lead to discomfort, such as pain, etc. in the laryngectomy patient.

The stop element provides, together with the first annular surface, sufficient support for a voice prosthesis after it has been placed on the head region of the rod in the rod-shaped device, wherein a wall of a flange on a voice prosthesis can or does come in contact with the first annular surface. As a result, the voice prosthesis made of a flexible, elastic material is stabilized by the support of this flange, and the stop element and the first annular surface prevent the retention element from being inserted too far in the interior of the voice prosthesis after it is placed thereon, thus damaging the actual valve in the interior of the voice prosthesis. The flange surface of the voice prosthesis that can bear on the first annular surface, faces the interior of the esophagus after it has been placed in the tracheoesophageal fistula, and is therefore not in contact with the upper surface thereof.

The rod in the rod-shaped device can be round, for example, but is preferably flattened, such that is has a substantially planar, flat upper and lower surface, which are connected to one another via a rounded transition. The rod has at least one, preferably at least two, more preferably at least three fastening elements for a fastening nipple on a voice prosthesis. The fastening elements can be in the form of keyholes. A keyhole fastening element comprises a circular part of the opening and an adjoining slotted part of the opening. A fastening nipple on a voice prosthesis can be inserted in the round part of the opening, and then secured in the slotted part of the keyhole fastening element. The rod of the rod-shaped device preferably comprises at least two keyhole fastening elements of this type. The rod of the rod-shaped device preferably comprises a second fastening element in the form of a projection. This projection is advantageously located on a planar, flat upper surface of the rod. This projection preferably has a round cross section, and is also advantageously in the form of a cylinder. Such a fastening element is used to secure the fastening nipple of the voice prosthesis to the rod of the rod-shaped device, in that an opening is formed in the fastening nipple, through which such a fastening element can be inserted.

In a particularly preferred embodiment there are exactly three fastening elements on the rod of the rod-shaped device of the insertion aid according to the invention for a fastening nipple of the voice prosthesis, which enable the attachment of different voice prostheses known from the prior art. There is preferably a first keyhole fastening element located on the first end of the rod, starting from the head region, forming the next element. After this, a cylindrical fastening element is preferably located on a planar, flat upper surface of the rod, wherein this can also be obtained with a round design of the rod. A second fastening element is located after this, toward the second end thereof, opposite the first end.

The second end of the rod advantageously has at least one gripping element, preferably at least two gripping elements. The gripping element is preferably in the form of a depression in the rod of the rod-shaped device. The gripping element preferably has fluting, such that it can be held securely with a finger of the user. At least a part of the surface of the gripping element preferably has such a fluting, and more preferably, at least a part of the surface, more preferably the entire surface, of the gripping element in the form of a depression on the gripping element has this fluting. In a particularly preferred embodiment, there are exactly two adjoining gripping elements on the second end of the rod of the rod-shaped device, wherein it is also preferred that these two gripping elements are in the form of a depression, and also preferably have a fluting over the entire surface of the depression.

The rod of the rod-shaped device also preferably has at least one marking element, preferably at least two marking elements. These marking elements are preferably adjacent to the at least one gripping element. The marking element preferably comprises a projection on the upper surface of the rod of the rod-shaped device, preferably a linear projection, located in a plane perpendicular to the longitudinal axis of the rod, on the upper surface thereof. An embodiment in which the linear projection of the marking element is located on a planar, flat upper surface of the rod is preferable. The marking element provides the user with information in particular regarding the position of a voice prosthesis on the insertion aid according to the invention. This preferably comprises, in addition to the rod-shaped device, at least one sleeve. After placing the voice prosthesis on the rod-shaped device of the insertion aid according to the invention, the rod-shaped device is inserted with the voice prosthesis into the sleeve. The voice prosthesis is then placed in a targeted manner in the tracheoesophageal fistula and inserted therein via an extraction region that tapers in comparison to the insertion region of the sleeve. The at least one marking element is used to determine the position of the voice prosthesis in this extraction region of the sleeve.

In a preferred embodiment, the first annular surface located in the head region of the rod of the rod-shaped device is formed by the stop element. The stop element is the first element of the head region facing the first end of the rod, and is also preferably located directly on the first end of the rod of the rod-shaped device. The stop element is preferably cylindrical. It is preferably rotationally symmetrical. A sheath surface of the stop element extends over the dimensions of the rod per se, in at least one direction, preferably in all directions. The first annular surface is also formed by a head surface of the cylindrical stop element.

The retention element is preferably in the form of a truncated cone according to the invention. The retention element is preferably rotationally symmetrical, and advantageously has a smaller radius or diameter than the first annular surface, starting from a head surface of the retention element. The head surface of the retention element in turn preferably forms a second annular surface. The retention element also preferably comprises a second annular surface. The retention element in the form of a truncated cone is preferably located in the head region such that the end surface with the smaller diameter is connected to an upper surface of the stop element forming the first annular surface. The head surface of the stop element in the form of a truncated cone with the greater diameter faces away from the stop element. The design of the retention element according to the invention can also be described as an inverted truncated cone, connected to the stop element.

In another preferred embodiment, there is a transition between the second annular surface and the outer surface of the retention element that forms a rim. The rim can be slightly rounded. This rim comes in contact with an inner wall of the shaft of the voice prosthesis, and bears on the shaft at the circumferential line formed by the rim. As a result, the rod-shaped device is securely retained in place and can nevertheless be easily removed after inserting a voice prosthesis in the tracheoesophageal fistula.

An angle $\alpha$ is preferably formed between the outer surface of the retention element and the second annular surface, in a range of approx. 50° to approx. 86°, more preferably in a range of approx. 65° to approx. 85°, and even more preferably in a range of approx. 72° to approx. 83°. As a result of this design of the retention element, when a voice prosthesis is placed on the head region of the rod-shaped device it is ensured that enough space is created between the outer surface and an inner wall of the shaft of the voice prosthesis, such that the insertion aid can be easily, and in particular painlessly, removed after placing the voice prosthesis in the tracheoesophageal fistula.

The head region also preferably comprises a pre-retention element. The pre-retention element is preferably adjacent to, preferably directly adjacent to the retention element. The pre-retention element is preferably in the form of a cylindrical rod, just like the stop element can also be in the form of a cylindrical rod. The diameter of the rotationally symmetrical pre-retention element is preferably smaller that that of the retention element. The diameter of the pre-retention element is also preferably smaller than a diameter defined by the rim of the retention element. The pre-retention element is also preferably taller than the stop element. The pre-retention element holds a voice prosthesis on the rod-shaped device, thus facilitating retention of the voice prosthesis for the user, in particular. The pre-retention element is of such a size that it does not become retained or fixed in the shaft of the voice prosthesis, but instead, the voice prosthesis is only loosely placed with its shaft on the pre-retention element.

In a preferred embodiment, the stop element and/or the pre-retention element is coaxial to the rod and the longitudinal axis thereof, wherein a central axis of the stop element and/or the pre-retention element is also preferably aligned with the longitudinal axis of the rod. The retention element is also preferably designed like the stop element and/or the pre-retention element, as described above.

In a particularly preferred embodiment, the head region of the rod-shaped device is formed by a cylindrical stop element, a truncated cone retention element directly adjoining it, and a cylindrical pre-retention element directly adjoining the retention element. The diameter of the retention element is preferably greater than the diameter defined by the rim of the retention element, which in turn is greater than the diameter of the cylindrical pre-retention element. The diameter of the first annular surface is preferably greater than the diameter of the second annular surface. The first annular surface is preferably formed by the stop element and the second annular surface is preferably formed by the retention element.

In a preferred embodiment, there is at least one material accumulation on the rod underneath the head region, preferably at least two material accumulations. The material accumulation is preferably formed when the rod is not round, but instead contains, in particular, a planar, flattened upper surface and lower surface, connected to one another by a rounded region. The material accumulation is located on the rod, starting from its planar, flat upper surface and lower surface, thus increasing its thickness. The material accumulation preferably extends to a lower surface of the stop element, directly adjacent thereto. The material accumulation provides the rod of the rod-shaped device with sufficient stability regarding the design of the head region, such that a voice prosthesis can be securely placed therein.

The insertion aid according to the invention also advantageously comprises a sleeve. The rod-shaped device can advantageously be inserted into this sleeve. The rod-shaped device is inserted in order to insert a voice prosthesis after the voice prosthesis has been placed in the head region of the rod-shaped device. The sleeve is used to aid in ensuring a safe insertion of the voice prosthesis for the user, e.g. the physician or patient. The sleeve is advantageously elastic at the extraction end. The voice prosthesis is ultimately inserted into the tracheoesophageal fistula through this extraction end, after passing through the sleeve. The extraction end is tapered to a greater extent than the upstream wall of the sleeve, which is slightly conical. As a result of the greater tapering, the flanges of the voice prosthesis are folded down to a greater extent prior to extraction through the opening in the extraction region of the sleeve, such that the voice prosthesis can be inserted through the surgical opening, which is smaller than the flanges on the voice prosthesis. The elastic design can be obtained through at least two, preferably at least three, more preferably at least four slits running in the direction of the longitudinal axis of the sleeve, formed in the extraction region of the sleeve. As a result, the regions lying between the slits, which are coaxial to the longitudinal axis of the sleeve, can be moved elastically, and can adapt to the shape of the voice prosthesis. An elastic design in the extraction region can preferably also be obtained by using an at least slightly elastic material for the sleeve. The sleeve is preferably made of an at least slightly elastic material at its extraction region, and also contains the aforementioned longitudinal slits. The extraction region particularly preferably has exactly three or four longitudinal slits, distributed over the circumference of the extraction region at an angle of 90° or 120° to one another, respectively. The extraction region is rounded at the opening thereof, in order to avoid injury when inserting the voice prosthesis in the tracheoesophageal fistula.

A receiving slit is particularly preferably formed in an insertion region of the sleeve, opposite the extraction region, into which the voice prosthesis can be inserted using the rod-shaped device. This enables a targeted folding of one, or preferably both, flanges of a voice prosthesis that is to be inserted into the sleeve via the rod-shaped device. The insertion region is preferably in the shape of a funnel, such that it facilitates the receiving and guidance of a voice prosthesis placed on a rod-shaped device. The wall of the sleeve is preferably conical, tapering from the insertion region toward the extraction region. As explained above, the extraction region itself is more conical than the conical wall between the insertion region and the extraction region. The slightly conical shape of the wall of the sleeve in the area between the insertion region and the extraction region pre-orients the voice prosthesis that is to be inserted into the tracheoesophageal fistula prior to extraction through the extraction region.

The present invention also relates to a rod-shaped device for a voice prosthesis, as explained above in conjunction with the insertion aid according to the invention. Reference is made in this regard to the explanations above. The present invention also relates to the use of an insertion aid according to the invention, and a rod-shaped device, as described above, for inserting a voice prosthesis in an opening between the trachea and esophagus, thus in a tracheoesophageal fistula.

BRIEF DESCRIPTION OF THE DRAWINGS

These and further advantages of the present invention shall be explained in greater detail in reference to the following figures. Therein.

DETAILED DESCRIPTION OF THE INVENTION

It should first be noted that the embodiments shown in the figures are not to be interpreted as limiting. Instead, the features described therein can be combined among one another and with the features described above to obtain further embodiments. By way of example, there can be just two fastening elements for a fastening nipple of a voice prosthesis, or there can also be more than three such fastening elements. These can also differ from one another, e.g. in the form of keyhole fastening elements or cylindrical projections. There can also be just one gripping depression for a gripping element, and just one marking element. An extraction region can also have more or fewer slits, or no slits if the extraction region is sufficiently elastic.

Lastly, it should be noted that the reference symbols in the descriptions of the figures and the claims do not limit the scope of protection for the present invention, but only refer to the embodiments shown in the figures.

Figure 1:
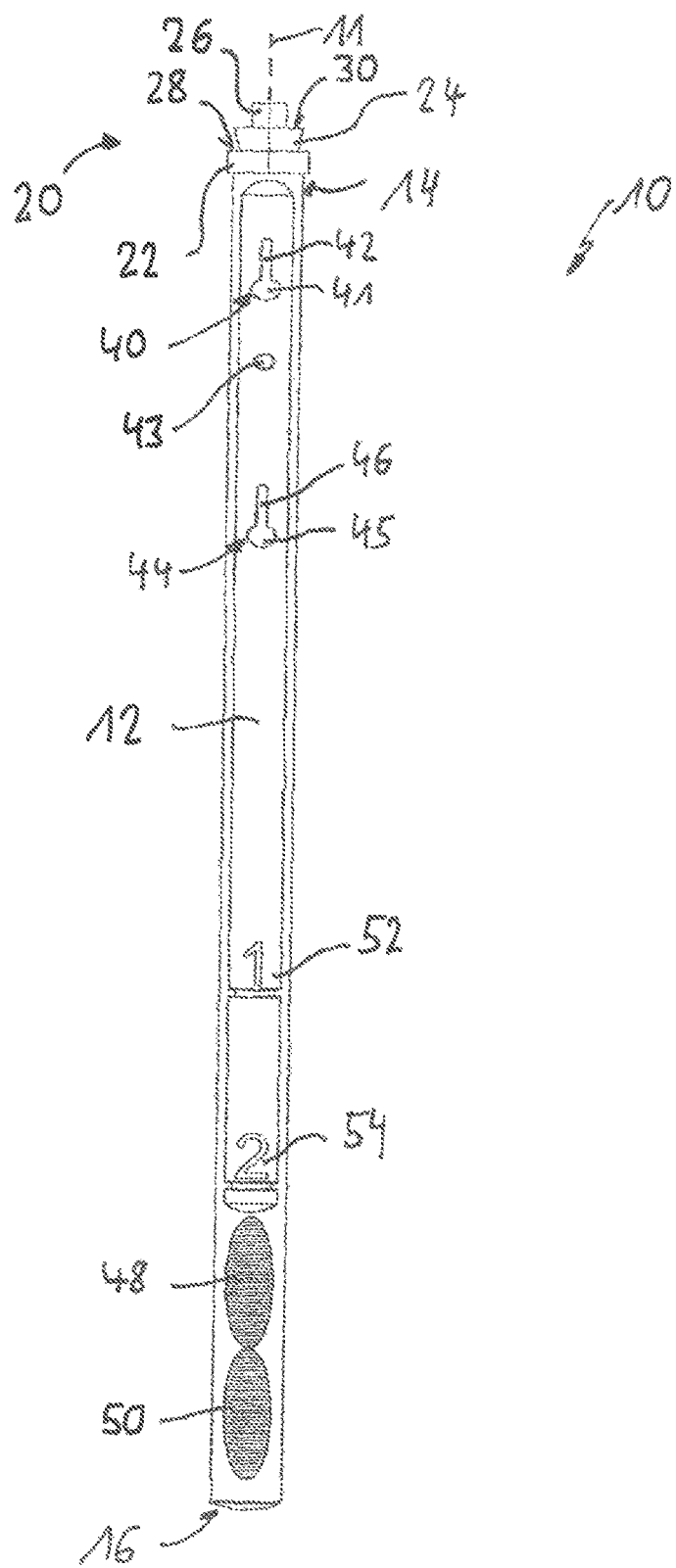
FIG. 1: shows a rod-shaped device according to the invention in a top view.

FIG. 1 shows rod-shaped device according to the invention in a top view, indicated as a whole with the reference symbol 10, which can be a component of the insertion aid according to the invention. The rod-shaped device 10 has a rod with a first end 14 and a second end 16. The rod 12 has two gripping elements 48 and 50 in the form of depressions near the second end 16, for fingers of the user, wherein the depressions have a fluting over more or less the entire surface. The rod 12 also has two marking elements 52 and 54, the design of which is explained in greater detail below in reference to FIG. 3. The rod 12 also has three fastening elements 40, 43, and 44. The fastening elements 40 and 44 are in the form of keyholes, each having a round opening part 41 and 45, and a slotted opening part 42 and 46, adjoining the round opening. There is a further fastening element 43 between the fastening openings 40 and 44, in the form of a cylindrical projection (see FIGS. 2 and 3).

A head region 20 of the rod-shaped device 10 is located directly on the first end 14, with a stop element 22, a directly adjacent retention element 24, and a pre-retention element 26 directly adjacent thereto. The stop element 22, the retention element 24, and the pre-retention element 26 are rotationally symmetrical and coaxial to the longitudinal axis 11 of the rod 12, wherein the central axes of the stop element 22, the retention element 24 and the pre-retention element 26 are aligned with the longitudinal axis 11 of the rod 12.

The stop element 22 forms a first annular surface 28 and the retention element 24 forms a second annular surface 30. The diameter of the stop element 22 is greater than the maximum diameter of the retention element 24, which in turn is greater than the diameter of the pre-retention element. The stop element 22 and the pre-retention element 26 are cylindrical. The retention element 24 is in the form of an inverted truncated cone.

Figure 2:
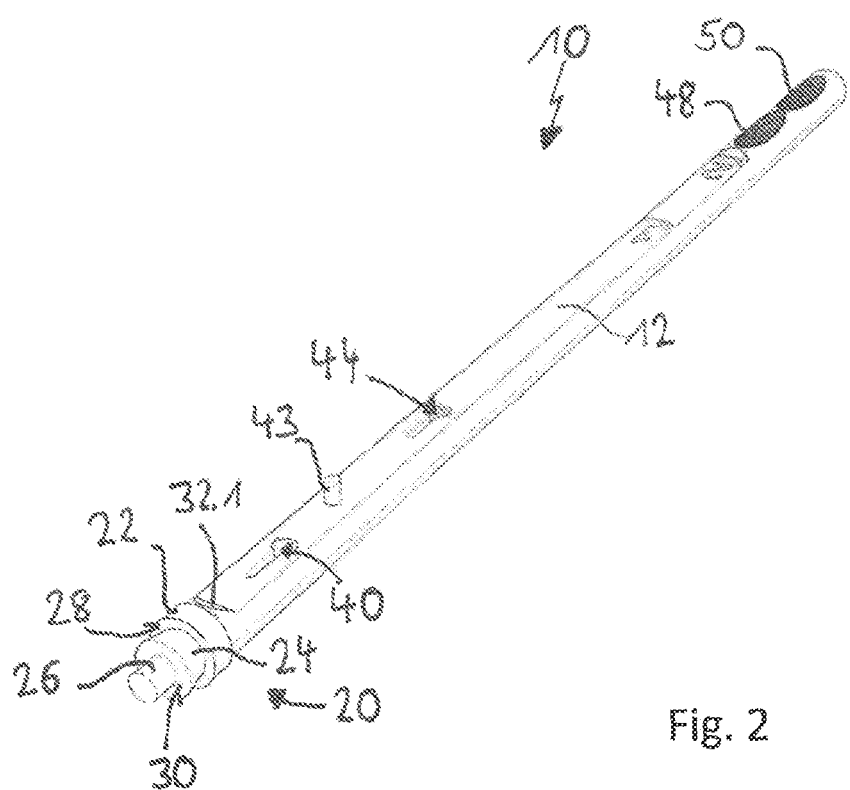
FIG. 2: shows the rod-shaped device according to FIG. 1 in a perspective view.

FIG. 2 shows the rod-shaped device 10 according to FIG. 1 in a perspective view, in which the design of the other fastening element 43 in the form of a cylindrical projection can be readily seen. The form of a first material accumulation 32.1 can also be readily seen. The rod 12 itself is flattened, containing a flat upper surface and an opposing corresponding lower surface, which are connected to one another via a rounded region. The material accumulation 32.1 increases in size, starting from an upper surface of the rod 12, toward the head region 20 of the rod-shaped device 10.

Figure 3:
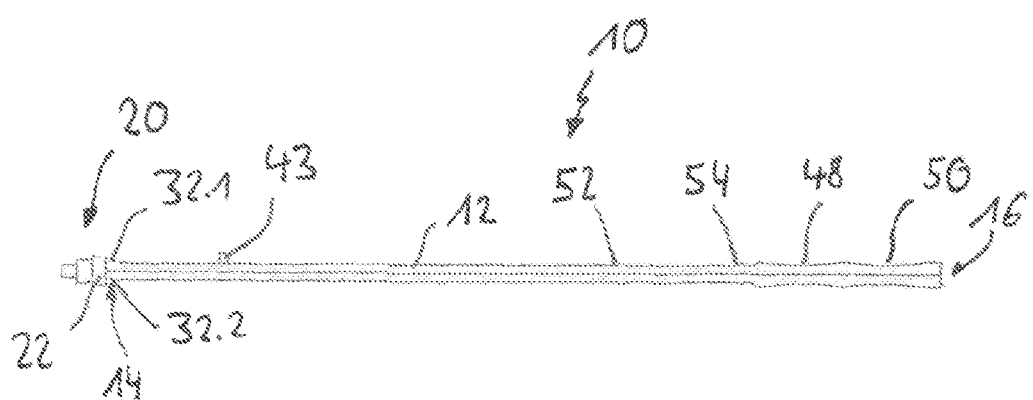
FIG. 3: shows the rod-shaped device according to FIG. 1 in a side view.

FIG. 3 shows a side view of the rod-shaped device according to FIG. 1, in particular the form of the first material accumulation 32.1 and a second material accumulation 32.2 opposite the first, on a lower surface of the rod 12. In particular, it can be readily seen in FIG. 3 that the two material accumulations 32.1 and 32.2 border directly on the stop element 22. The design of the two marking elements 52 and 54 can also be derived from FIG. 3. It can be readily seen that these are formed as linear projections on the upper surface and lower surface of the rod 12, wherein these linear projections run in a plane perpendicular to the longitudinal axis 11 of the rod 12 (see FIG. 1).

Figure 4:
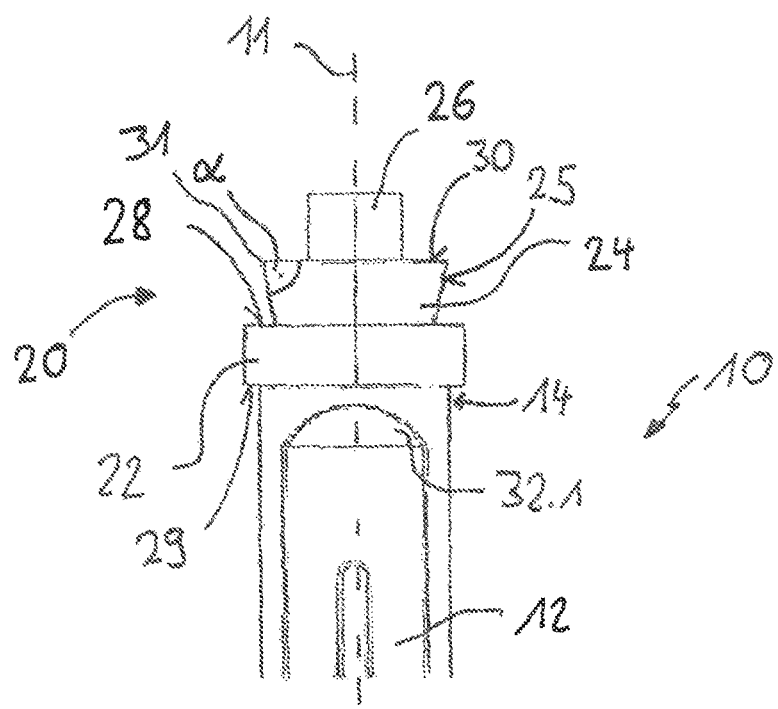
FIG. 4: shows the head region of the device according to FIG. 1 in an enlarged view.

FIG. 4 shows a detail of the design of the head region 20 of the rod-shaped device 10 according to FIG. 1. The first material accumulation 32.1 on the first end 14 of the rod 12 borders directly on the stop element 22, more precisely on a lower surface 29 thereof. The retention element 24 forms an angle α of approx. 80° between the second annular surface 30 and an outer surface 24 thereof. A rim 31 is formed between the second annular surface 30 and the outer surface 25 of the retention element 24, the linear circumference of which interacts with an inner wall of a shaft in such a voice prosthesis 80 when the voice prosthesis 80 (see FIGS. 9 to 13) is placed on the rod-shaped device 10, thus retaining it in place. The inverted truncated cone shape of the retention element 24 results in the retention of a voice prosthesis 80 only above the region of the circumference of the rim 31 on the retention element, such that the rod-shaped device 10 can be removed painlessly after inserting the voice prosthesis 80.

Figure 5:
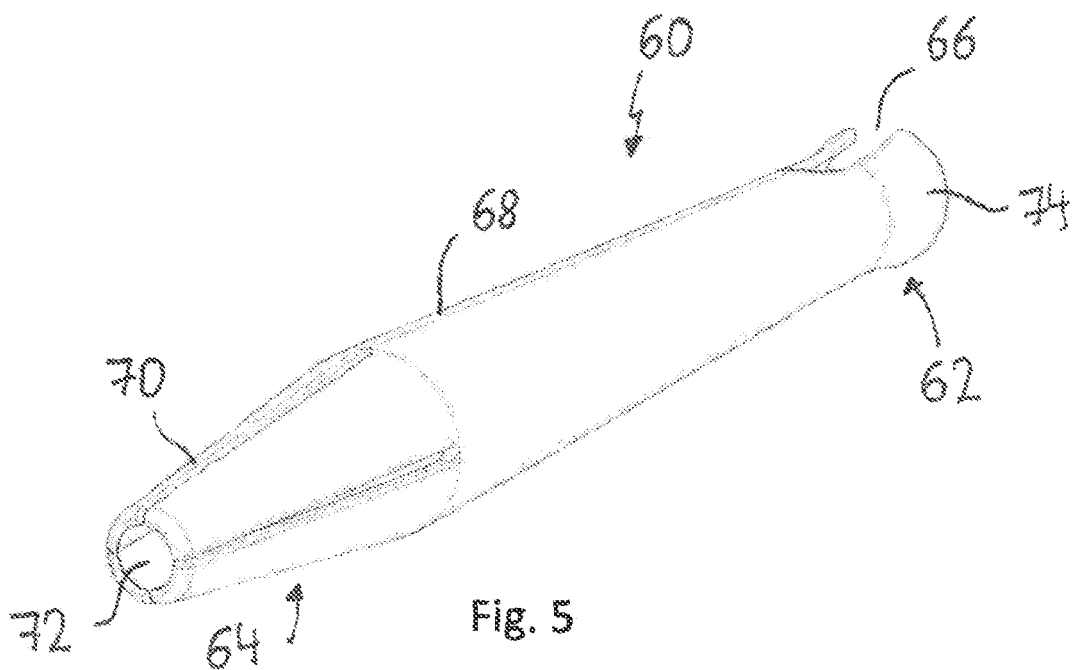
FIG. 5: shows a sleeve for the insertion aid according to the invention, in a perspective view.

FIG. 5 shows a sleeve 60 in a perspective view, which is also to be regarded as belonging to the present patent application. This sleeve 60 has an extraction region 64 and an insertion region 62. The insertion region 62 has a receiving slit 66. The insertion region 62 also forms a funnel 74, wherein the receiving slit 66 is substantially located in the funneled portion 74 of the insertion region 62. The extraction region 64 of the sleeve is located at the end opposite the insertion region 62. This is more conical than the wall 68 in the region between the insertion region 62 and the extraction region 64, wherein the wall 68 is also slightly conical, starting from the insertion region 62 and tapering toward the extraction region 64. The extraction region 64 has a total of four linear slits 70 and comprises a rounded extraction opening 62.

Figure 6:
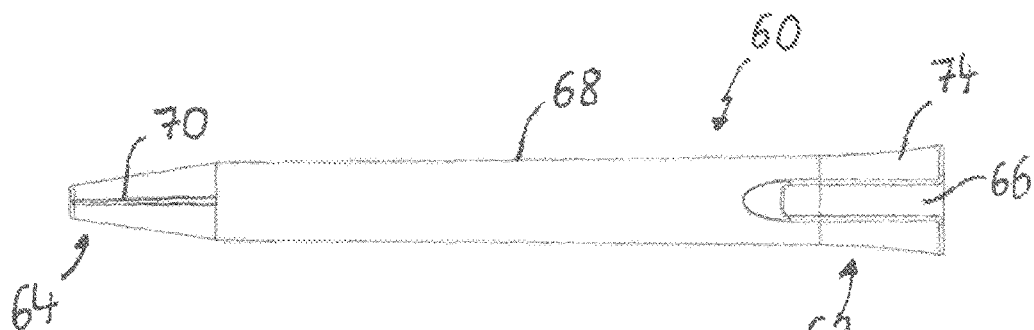
FIG. 6: shows the sleeve according to FIG. 5 in a top view.

FIG. 6 shows a top view, illustrating the sleeve 60 according to FIG. 5, wherein the form of the receiving slit 64 in the insertion region 62 can be readily seen in particular in the funnel region 74.

Figure 7:
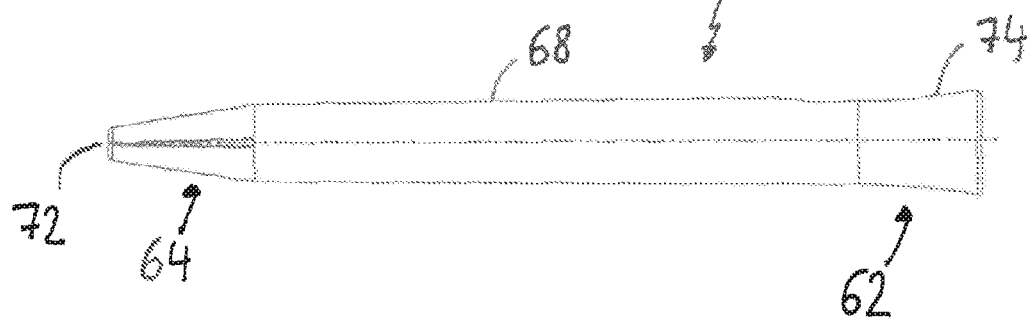
FIG. 7: shows the insertion aid according to FIG. 5, in a sectional view.

It can be derived from FIG. 7, which shows a cross section through the sleeve 60, that the wall 68 is slightly conical, tapering from the insertion region 62 toward the extraction region 64, and exhibiting a more or less uniform material thickness over its entire length.

Figure 8:
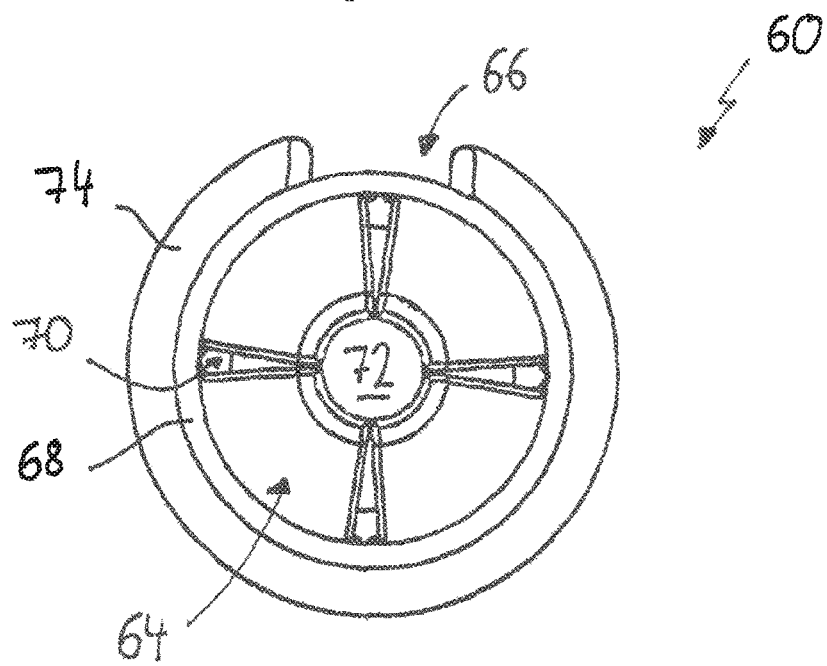
FIG. 8: shows the insertion aid according to FIG. 5 in an enlarged front view.

FIG. 8 then shows an enlarged frontal view of the sleeve 60 according to FIG. 5, wherein the arrangement of the four slits 70 and their path toward the opening 70 in the extraction region 64 can be readily seen. The slightly conical shape of the wall 68 and the funnel 74 can also be readily seen therein.

Figure 9:
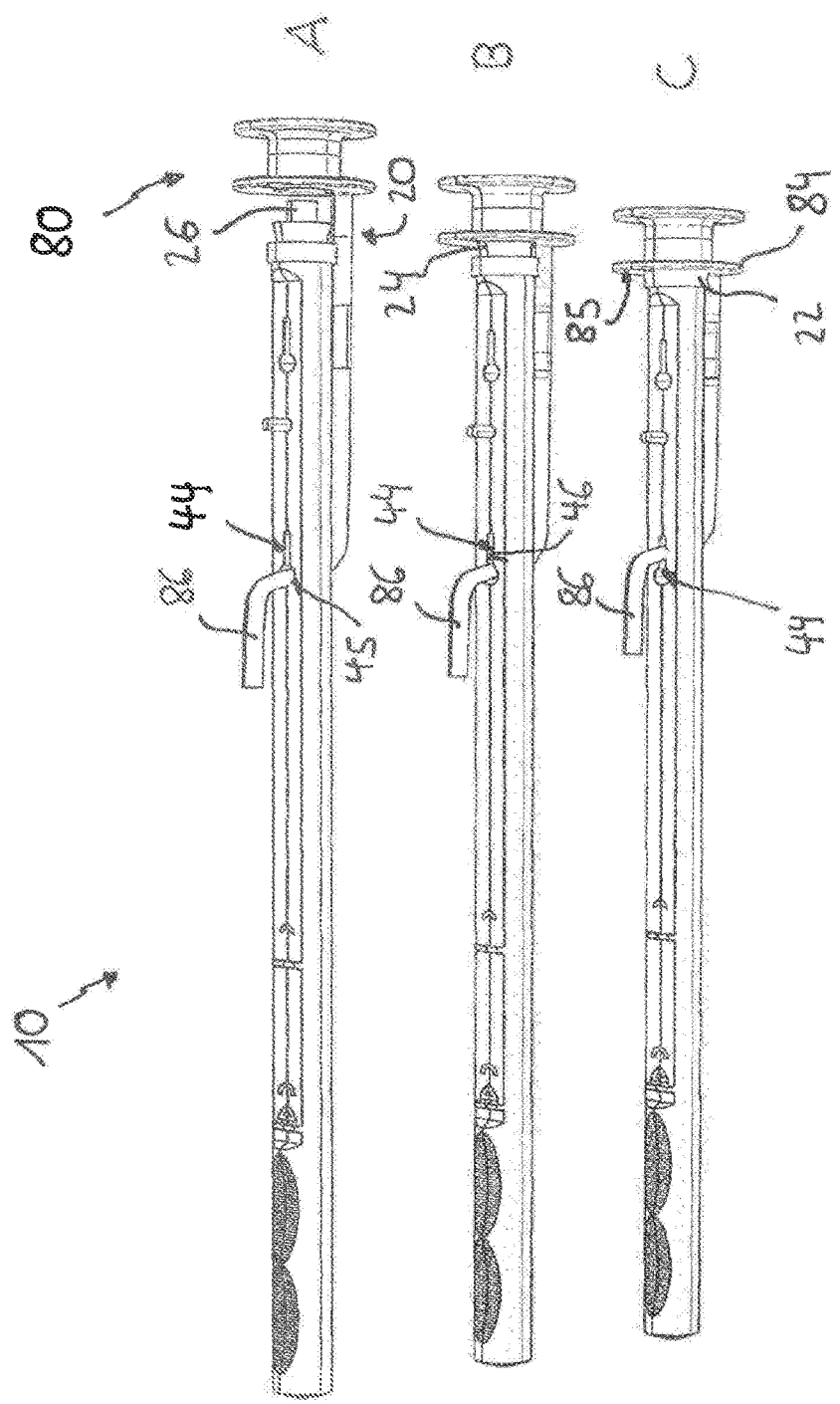
FIG. 9: shows three states of the placement of a voice prosthesis on the rod-shaped device according to FIG. 1.

FIG. 9 shows an initial position A of the placement of a voice prosthesis 80 on the rod-shaped device 10, wherein the voice prosthesis 80 has a fastening nipple 86 that is inserted through the keyhole fastening element 44 at its round opening 45. The position B shows a retained position in which the voice prosthesis 80 has a dedicated retention element 24, and is retained in place therewith. As a result of this retention, the fastening nipple 86 on the voice prosthesis 80 can be secured in the keyhole fastening element 44, in particular in the slotted portion 46 thereof. Position C shows the stopped and retained position of the voice prosthesis 80, wherein a flange 84 bears with its outer surface 85 directly on the first annular surface 28 of the stop element 22.

Figure 10:
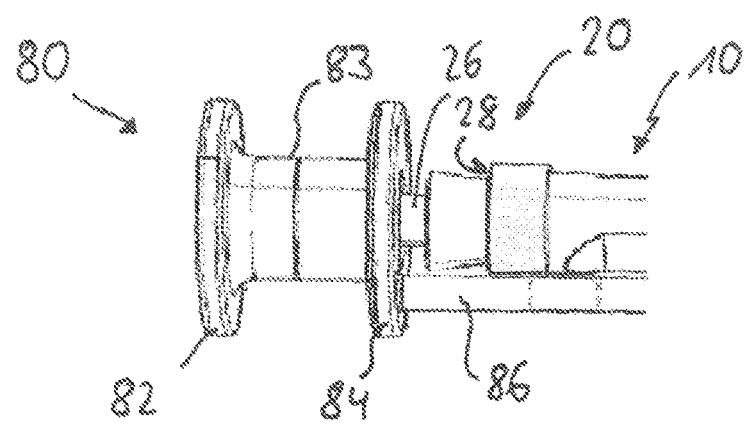
FIG. 10: shows a detail of a placement of a voice prosthesis on the rod-shaped device according to FIG. 1 (pre-retention position)
Figure 11:
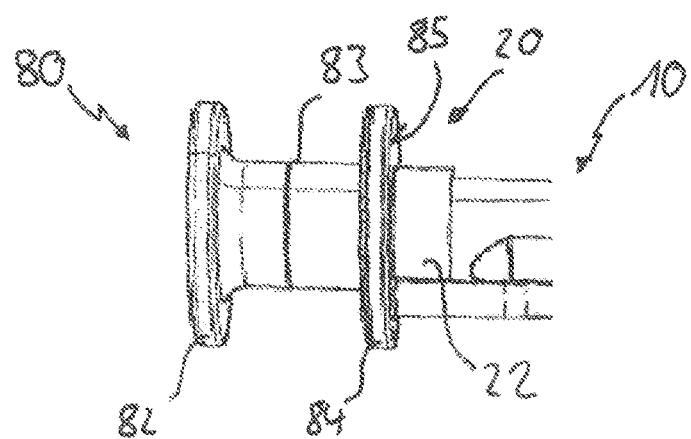
FIG. 11: shows a second placement of a voice prosthesis on the rod-shaped device according to FIG. 1 (retained and stopped position)

FIGS. 10 and 11 show a position between A and B as well as the position C according to FIG. 9 in detail. In particular, the voice prosthesis 80 is more closely defined as comprising a flange 82 in addition to the flange 84 facing the rod-shaped device 10, wherein there is a shaft 83 between the two flanges 82 and 84. The flange 82 must be folded in a targeted manner by means of the sleeve and the rod-shaped device 10, so that it can pass through the opening provided in the tracheoesophageal fistula. The pre-retention or pre-retention by the pre-retention element 26 can be readily seen, in particular such that it does not come in contact with an inner wall of the shaft 83. FIG. 11 shows the position C, described above in reference to FIG. 9, of the stopped and retained position with the interaction of the stop element 22 and the flange 84 of the voice prosthesis 80.

Figure 12:
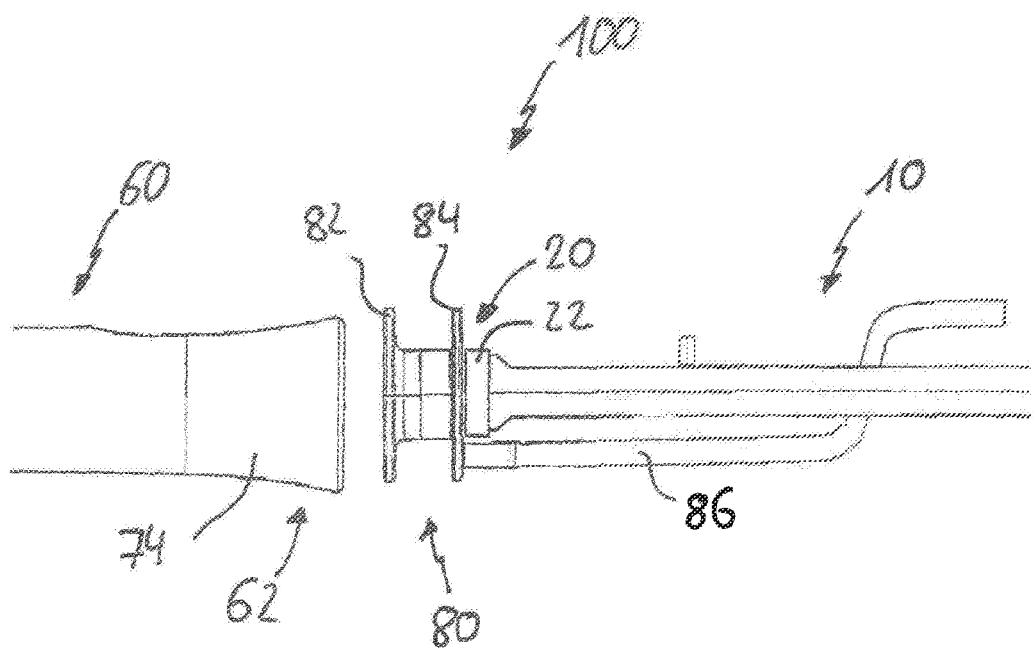
FIG. 12: shows a partial view of an insertion aid according to the invention, comprising a rod-shaped device and a sleeve, wherein the rod-shaped device supports a voice prosthesis.

FIG. 12 shows the insertion aid 100 according to the invention with the rod-shaped device 10 and the sleeve 60. The rod-shaped device 10 has a voice prosthesis in the retained and stopped position, this being shortly before insertion into the funnel 74 of the insertion region 62 of the sleeve 60.

Figure 13:
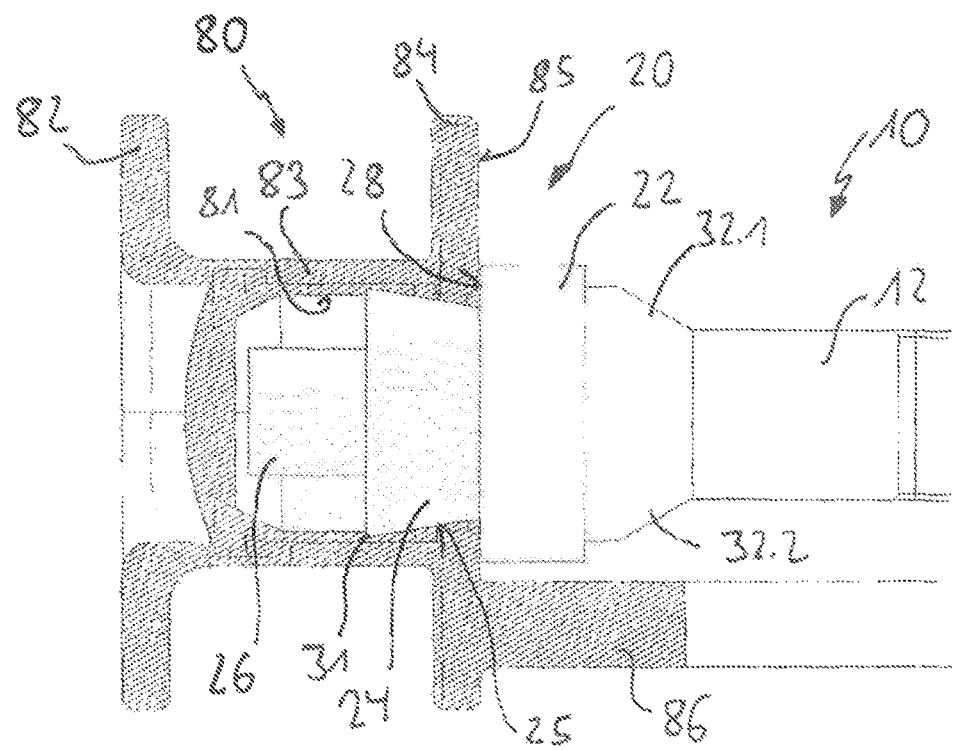
FIG. 13: shows a sectional view of the placement of a voice prosthesis on the rod-shaped device according to FIG. 1 (retained and stopped position).

FIG. 13 shows the stopped and retained position according to FIG. 11 in a cutaway view. It can be readily seen that the rim 31 of the retention element 24 pushes into the material of the shaft 83, or the shaft stretches over the circumference of the rim 31, thus retaining the voice prosthesis 80 in place with the rod-shaped device 10. There is also a certain amount of retention on the inner wall 81 of the shaft 83 in the region of the outer wall, adjacent to the rim 31, through the retention element 24. FIG. 13 illustrates a schematic view that does not entirely correspond to the actual retained position. This is because the material of the voice prosthesis 80, and in particular the shaft 83 thereof, is relatively soft and elastic, and is normally made of medical silicone. The corresponding flexibility of the shaft material, in particular the inner wall 81 of the shaft 83 as well, is not shown in FIG. 13. This gives the impression that in the region of the outer surface 25 of the retention element 24 it bears over its circumference on the inner wall 81 of the shaft 83. In fact, there is substantially only a linear contact, more or less along the circumference of the rim 31 of the retention element 24. The contact between the outer surface 85 of the flange 84 with the first annular surface 28 of the stop element 22, as well as the form of the first and second material accumulations 32.1 and 32.2 can also be readily seen in FIG. 13.

A universally usable insertion aid and a universally usable rod-shaped device are obtained through the present invention, with which voice prostheses of different designs and from different manufacturers can be inserted in the tracheoesophageal fistula. In particular, the rod-shaped device advantageously has a retention element, by means of which a secure and sufficiently firm retention of the voice prosthesis in the tracheoesophageal fistula is ensured, in particular using the sleeve. In particular in the embodiment with a retention element in the head region of the rod-shaped device, with which only a more or less linear contact is obtained between a circumferential rim 31 and an inner wall of the shaft, in addition to a secure retention, a hopefully painless removal of the insertion aid can take place after inserting the voice prosthesis.

The invention claimed is:

1. An insertion aid for a voice prosthesis, comprising a rod-shaped device with a head region located on a first end of a rod, comprising a stop element for a voice prosthesis and an adjoining retention element positioned along a longitudinal axis of the rod toward the first end relative to the stop element in the form of an inverted truncated cone for a voice prosthesis, wherein a head surface of the retention element, formed as a truncated cone, is arranged facing away from the stop element with its larger diameter, the stop element having a greater diameter than the retention element wherein a first annular surface is formed between the stop element and the retention element, which extends radially in relation to the longitudinal axis of the rod.

2. The insertion aid according to claim 1, wherein the first annular surface is formed by the stop element.

3. The insertion aid according to claim 1, wherein the retention element comprises a second annular surface.

4. The insertion aid according to claim 3, wherein a rim is formed between the second annular surface and an outer surface of the retention element.

5. The insertion aid according to claim 3, wherein an angle $\alpha$ is formed, in a range of approx. 50° to approx. 86°, between an outer surface of the retention element and the second annular surface.

6. The insertion aid according to claim 3, wherein the first annular surface has a greater diameter than the second annular surface.

7. The insertion aid according to claim 1, wherein the head region comprises a pre-retention element adjacent to the retention element.

8. The insertion aid according to claim 1, wherein the stop element and/or a pre-retention element are cylindrical.

9. The insertion aid according to claim 1, wherein the stop element and/or the pre-retention element are coaxial to the rod and the longitudinal axis running through it.

10. The insertion aid according to claim 1, wherein at least one material accumulation is beneath a gripping region on the rod.

11. The insertion aid according to claim 10, wherein the at least one material accumulation borders directly on a lower surface of the stop element.

12. The insertion aid according to claim 1, further comprising a sleeve, into which the rod-shaped device can be inserted.

13. The insertion aid according to claim 12, wherein the sleeve is elastic in an extraction region.

14. The insertion aid according to claim 13, further comprising at least one receiving slit for a voice prosthesis in an insertion region.

15. The insertion aid according to claim 13, wherein a wall of the sleeve tapers conically toward the extraction region.

16. An insertion aid for a voice prosthesis, comprising a rod-shaped device with a head region located on a first end of a rod, comprising a stop element for a voice prosthesis and an adjoining retention element in the form of an inverted truncated cone for a voice prosthesis, the stop element having a greater diameter than the retention element wherein a first annular surface is formed between the stop element and the retention element, which extends radially in relation to a longitudinal axis of the rod and wherein the retention element comprises a second annular surface.

17. An insertion aid for a voice prosthesis, comprising a rod-shaped device with a head region located on a first end of a rod, comprising a stop element for a voice prosthesis and an adjoining retention element in the form of an inverted truncated cone for a voice prosthesis, the stop element having a greater diameter than the retention element wherein a first annular surface is formed between the stop element and the retention element, which extends radially in relation to a longitudinal axis of the rod and wherein the head region comprises a pre-retention element adjacent to the retention element.

\* \* \* \* \*